United States Patent
Lemme

(10) Patent No.: US 8,715,176 B2
(45) Date of Patent: May 6, 2014

(54) METHOD FOR AUTOMATED DELIVERY OF PERSONALIZED PHYSICAL THERAPY SESSIONS TO TREAT PAIN

(76) Inventor: John P. Lemme, Mission Viejo, CA (US)

( * ) Notice: Subject to any disclaimer, the term of this patent is extended or adjusted under 35 U.S.C. 154(b) by 1385 days.

(21) Appl. No.: 11/669,278

(22) Filed: Jan. 31, 2007

(65) Prior Publication Data

US 2007/0179816 A1 Aug. 2, 2007

Related U.S. Application Data

(60) Provisional application No. 60/743,196, filed on Jan. 31, 2006.

(51) Int. Cl.
| | |
|---|---|
| *A61B 5/00* | (2006.01) |
| *G06F 19/00* | (2011.01) |
| *G06Q 50/24* | (2012.01) |
| *G06T 13/40* | (2011.01) |
| *G06T 13/00* | (2011.01) |
| *A63B 71/00* | (2006.01) |
| *G06Q 50/00* | (2012.01) |

(52) U.S. Cl.
CPC ........ *G06F 19/3475* (2013.01); *G06F 19/3487* (2013.01); *G06F 19/3418* (2013.01); *G06F 19/363* (2013.01); *G06F 19/3406* (2013.01); *G06F 19/322* (2013.01); *G06F 19/3481* (2013.01); *G06Q 50/24* (2013.01); *G06T 13/40* (2013.01); *A63B 71/00* (2013.01)
USPC ............... 600/300; 345/581; 345/661; 705/3; 715/716; 715/757; 715/762; 482/8

(58) Field of Classification Search
USPC ............. 702/85, 94, 108, 122, 127, 150, 166, 702/167, 183, 188; 345/418, 619, 620–629, 345/634, 501; 434/328, 307 R, 247, 118
See application file for complete search history.

(56) References Cited

U.S. PATENT DOCUMENTS

| 5,080,109 A | * | 1/1992 | Arme, Jr. ........................ 600/595 |
| 6,007,459 A | * | 12/1999 | Burgess ............................ 482/4 |

(Continued)

FOREIGN PATENT DOCUMENTS

| JP | 2002346012 | 12/2002 |
| WO | 03027936 | 4/2003 |

OTHER PUBLICATIONS

Hewes G. W., "World distribution of certain postural habits", American Anthropologist, 1955, vol. 57, issue 2, p. 231-244. p. 241, figure 1.*

(Continued)

*Primary Examiner* — Bill Thomson
*Assistant Examiner* — Marie Archer
(74) *Attorney, Agent, or Firm* — Barlow, Josephs & Holmes, Ltd.

(57) ABSTRACT

A user directed interactive method and system for implementing customized therapy routines. The method and system obtains relevant information from a user via an interactive questionnaire and via digital therapeutic techniques to evaluate the user's pain and provide a customized treatment regimen. The user then implements the custom treatment regimen in order to return their body to proper alignment thereby bringing about a state of muscular and internal balance to the individual naturally. In this manner, the method and system of the present invention replicates the process of in-clinic and video therapy programs while delivering customized therapy sessions and long-term therapy programs based on the user's individual needs via an electronic medium that is completely automated without the need for professional intervention, evaluation, or correspondence of any kind.

12 Claims, 14 Drawing Sheets

(56) References Cited

U.S. PATENT DOCUMENTS

| | | |
|---|---|---|
| 6,269,339 B1 | 7/2001 | Silver |
| 6,514,219 B1 * | 2/2003 | Guimond et al. ............. 600/595 |
| 7,311,666 B2 * | 12/2007 | Stupp et al. .................. 600/300 |
| 2002/0082143 A1 * | 6/2002 | Leeds ............................... 482/1 |
| 2002/0107707 A1 * | 8/2002 | Naparstek et al. ................ 705/3 |
| 2003/0023461 A1 * | 1/2003 | Quintanilla et al. ............. 705/3 |
| 2003/0120515 A1 | 6/2003 | Geller |
| 2004/0010420 A1 * | 1/2004 | Rooks ............................... 705/2 |
| 2004/0267565 A1 | 12/2004 | Grube |
| 2005/0043969 A1 | 2/2005 | Sarel |
| 2005/0147955 A1 | 7/2005 | Giacchetti |
| 2005/0195077 A1 | 9/2005 | McCulloch et al. |
| 2005/0228691 A1 | 10/2005 | Paparo |
| 2005/0240434 A1 | 10/2005 | Wooten et al. |
| 2006/0015016 A1 | 1/2006 | Thornton |
| 2006/0108851 A1 * | 5/2006 | Tsutsui et al. ................ 297/410 |
| 2006/0161455 A1 | 7/2006 | Anastasia |
| 2006/0178907 A1 | 8/2006 | Humble |
| 2007/0083384 A1 * | 4/2007 | Geslak et al. ..................... 705/2 |

OTHER PUBLICATIONS

Whitmore in Whitmore, M. et al., "NASA technical paper 3657: The evolution of the Posture Video Analysis Tool™ (PVAT)", Nov. 1996 (publication is available from the NASA Center for AeroSpace Information, 800 Elkridge Landing Road, Linthicum Heights, MD 21090-2934, (301) 621-0390).*

NPL_PosturePro—Commercially available software system for posture analysis (NPL_PosturePro.pdf).*

NPL_therapysolutions—Evidence of availability of online services for pain relief as of 2005. (NPL_therapysolutions.pdf).*

* cited by examiner

THERAPY SOLUTIONS
Your answer to chronic pain

My Treatment:
My Profile
Get New Therapy
My Therapy
My Progress
My Photos
Logout

Access Privilege:
Client Routines
Notes
Suggestions
New Client
Edit Client
Complimentary for client
General routines
Add new exercise
Exercises list
Statistics
E-mail office Page 4 of 10                                    Member _____

Question 6
10 —— What activities do you currently enjoy OR would participate in if pain was not a factor?

☐ Aerobics
☐ Baseball/Softball
☐ Basketball
☐ Cycling/Mountain Biking
☐ Football
☐ Golf
☐ Jog/Run
☐ Weight Lifting
☐ Rowing/Kayaking
☐ Skating
☐ Skiing/Snowboarding
☐ Soccer
☐ Swimming
☐ Tennis
☐ Volleyball
☐ Walk/Hike
☐ Water Activities
☐ Others
☑ None of the above

[Back]  [Next]

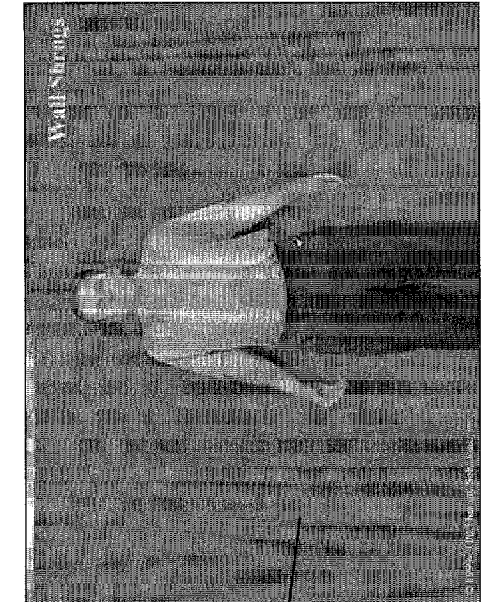
FIGURE 8

METHOD FOR AUTOMATED DELIVERY OF PERSONALIZED PHYSICAL THERAPY SESSIONS TO TREAT PAIN

CROSS-REFERENCE TO RELATED APPLICATIONS

This application is related to and claims priority from earlier filed U.S. Provisional Patent Application No. 60/743,196, filed Jan. 31, 2006, the contents of which are incorporated herein by reference.

BACKGROUND OF THE INVENTION

The present invention relates generally to an automated system for the delivery of personalized therapy sessions. More specifically, the present invention relates to an automated system whereby the user enters a variety of information related to their particular condition and provides various photographs and/or video clips that are in turn analyzed by the system to develop a personalized therapy routine for the user. The present invention is particularly, but not exclusively, useful as an automated method for creating a customized therapeutic exercise regimen developed by an expert system called the Anatomical Pain Elimination Expert System (APEX™) (APEX is a trademark of Therapy Solutions, Inc.) which is based on a set of rules via algorithms with complex patterns. The system immediately delivers a visual presentation of a physical therapy routine for an individual that can be viewed over the Internet. The system also allows for manual creation and delivery of therapeutic exercise via the Internet, called the Physical Therapy Expert System (PTEX™) (PTEX is a trademark of Therapy Solutions, Inc.) and fitness regimens for an individual that can also be viewed over the Internet, called the Fitness Expert System (FITEX™) (FITEX is a trademark of Therapy Solutions, Inc.).

Our bodily systems depend on motion for survival, yet human movement has changed and dramatically decreased over the past few centuries. With the onset of the industrial revolution, humans have witnessed large scale changes in communication beginning with the invention of the wireless telegraph and have further experienced a transformation in both our social and movement patterns as a result of the invention of the automobile. Then, during the real technology revolution at the end of the 20th century, the pace of human life and interaction quickened, but not the pace of the human feet. In general all of the advances, and especially the technological advances, that have come to us thought the beginning of the industrial revolution have developed societies that do not require sufficient movement by the average person. The difficulty is that as adequate movement ceases to exist, the postural and structural muscles of the body deteriorate. As a result, these muscles become dysfunctional and our structural integrity is compromised. The body then experiences compensations, limitations, and a vast number of ailments, which all compound to affect physical and mental performance. Fortunately, the body is a highly integrated structure and has a tremendous capacity for self-healing. Unfortunately, most modern medical treatments merely treat the site of pain while the use of drugs, surgical procedures, and many forms of therapeutic treatments often fail to address the causes of musculoskeletal pain. Thus, any possible symptom relief is only temporary, while the misalignments and dysfunctions remain.

The implementation of a physical therapy routine for remedying the various symptoms suffered by an individual is well known in the prior art and typically consists of a series of physical exercises. The exercises are usually prescribed and assigned to an individual by physical therapists for rehabilitation from a specifically identified disease and/or injury. When determining a proper routine, the physical therapist or exercise instructor also needs to account for individual factors such as age, fitness level, and medical history, in addition to the type of diseases or injury, the individual may be experiencing.

Once the physical therapy routine or work routine is prescribed, the physical therapist or exercise instructor must make sure the individual understands how to correctly accomplish the physical exercises in the routine. To do this, the physical therapist or exercise instructor will typically demonstrate the exercises to the individual and provide written instructions for subsequent reference. Often, however, this process is an inefficient use of the time of the physical therapist, particularly if the routine is lengthy and involved. Further, even though the individual may initially understand the entire routine, the individual may eventually forget how to correctly perform certain exercises in the routine over time.

Standardized videotapes and other well known technologies for visual presentations such as CD ROM and DVD that provide a visual presentation of physical exercises for muscle tone and weight reduction are known in the prior art as well, and also provide a means for reducing the therapist time required for proper instruction. These standardized visual presentations, however, typically assume that the person viewing the visual presentation and performing the exercises is a completely healthy person. Therefore, they do not account for the age, fitness level or physical malady of the individual that requires therapy. Moreover, for various reasons, other physical activities such as occupational therapy, athletic training programs and yoga exercises are subject to these same concerns.

In an attempt to overcome some of the shortcomings of the prior art self-directed systems, a number of non-interactive medical systems have been created to streamline the diagnostic process. Generally these systems are developed as guides that must be implemented by medical professionals For example, U.S. Pat. No. 4,130,881 to Haessler et al. discloses a medical diagnostic tool for health care professionals comprising a means for automated medical history taking. Haessler discloses the use of automated logic, wherein the questions asked are dependent on the patient's responses to prior questions.

U.S. Pat. No. 4,872,122 to Autschuler et al. discloses an interactive statistical system and method for predicting expert decisions. In practice, this system analyzes several input responses, by utilizing statistical analysis and preprogrammed expert opinions, to determine a diagnosis.

U.S. Pat. No. 5,025,374 to Roizen et al. discloses a device which is used to record patient history. Answers to a set of medical questions are used by the device to select medical or it pre-operative tests.

U.S. Pat. No. 5,235,510 to Umata et al. discloses a picture archiving communication lot system that records and stores various digital image data. In use, a patient is examined by way of a medical imaging device. The image is digitized and thereafter stored in a database with other relevant patient attributes. At a later time, medical personnel retrieve the image and other attributes at a remote workstation.

There is therefore a need for a system that allows a user to automatically input personal information regarding their condition to obtain a customized therapy routine. There is a further need for a method of creating a visual presentation of a work, exercise or physical therapy routine for an individual that customizes the visual presentation according to the specific performance capabilities of the individual. There is still a further need for a method for creating a visual presentation of a work, exercise or physical therapy routine that can be customized and delivered to an individual over the Internet, in a printout, on a CD or on a videotape. Finally, there is a further need for a method for creating a customized visual presentation of a work, exercise or physical therapy routine that is effectively easy to operate, relatively simple to manufacture, and comparatively cost effective.

BRIEF SUMMARY OF THE INVENTION

In this regard, the present invention provides for a user directed interactive method and system for implementing customized therapy routines. The method and system of the present invention is an innovative technique through which a user is enabled to evaluate and treat physical pain using a customized regimen. This form of therapeutic self-exercise restores optimum anatomical, physiological and neurological function to the human body. Simply put, a user can employ the system and method of the present invention in order to return their body to proper alignment, thereby bringing about a state of muscular and internal balance to the individual naturally.

Unlike practices such as physical therapy, massage therapy, chiropractic and other pain-treatment therapies, the system and method of the present invention does not use hands-on manipulations, drugs, machines or physical agents. The invention herein helps change posture, symptoms, and lives, by putting control of one's health back into the hands of the individual rather than creating dependence on the practitioner or system. Furthermore, the present system utilizes digital therapeutic techniques to assist in better directing the proper selection of a treatment regimen. This is a key factor that allows the present pain elimination and condition prevention programs to be electronically distributed. It further allows the method and system of the present invention to replicate the process of in-clinic and video therapy programs offered at the Applicant's facility by providing personalized sessions based on the Anatomical Pain Elimination Expert System (APEX™). These one-on-one therapy sessions are created on demand to meet each individual's specific physical needs.

The method and system of the present invention is implemented through a user interface that gives the user a series of simple exercises specifically tailored to their needs based on a questionnaire that they complete. An intelligent evaluation system then determines, based on the user input answers, the probable muscle dysfunctions and imbalances that are causing the user's symptom(s). The system then instantly provides the user with a therapy routine to follow in order to restore them to health.

One of the keys of the system of the present invention is the user interface whereby a user is prompted to register for access to the site and then is asked to build a personal profile through an interactive questionnaire that requests personal data such as age, weight, and sex, identification of the problem or symptom by selecting body areas, rating the severity of the pain or problem, identifying posture types using the specifically categorized and designed postural images, identifying posture types using the personalized postural image upload interface, identifying lifestyle issues, as well as listing how long the symptom has existed, when it first appeared, what body positions and activities make it worse, the symptom's affect on work and personal life including days missed from work, listing modalities, practitioners, and assessments for symptoms, listing medications both over-the-counter and prescription being taken for symptoms, listing diagnosis, diagnostic tests, and surgeries for symptoms, listing prognosis for symptom and whether or not surgery has been recommended, and understanding of overall physical condition and why the pain symptoms exist. Upon completing the interactive questionnaire, the system, through a series of thousands of rules via algorithms and complex patterns, selects a coordinated series of predefined therapy routines designed to systematically correct posture and muscular imbalances and relieve symptoms.

In light of the above, it is an object of the present invention to provide a method for creating a visual presentation of a work, exercise or physical therapy routine for an individual that customizes the visual presentation according to the specific performance capabilities of the individual. It is another object of the present invention to provide a method for creating a visual presentation of a work, exercise or physical therapy routine that can be delivered to an individual over the Internet, in a printout, on a CD or on videotape. Yet another object of the present invention is to provide a method for creating a customized visual presentation of a work, exercise or physical therapy routine, athletic training program, yoga or other exercise-based regimen that selectively retrieves a plurality of digital excerpts of specific exercises from an archive and collates these excerpts to demonstrate the routine. It is another object of the present invention to provide a method for creating a customized visual presentation of a work, exercise or physical therapy routine that is effectively easy to operate, relatively simple to manufacture, and comparatively cost effective.

These together with other objects of the invention, along with various features of novelty that characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In the drawings which illustrate the best mode presently contemplated for carrying out the present invention:

FIG. 1 is a screenshot representing a sample of an initial input screen in the system of the present invention;

FIG. 3-6 are screenshots representing a sample of an interactive questionnaire that is completed by the user for determining the user's physiological needs;

FIG. 7 is a screenshot representing a sample screen wherein a user identifies the best representation of their current posture;

FIG. 8 is a screenshot representing a sample exercise that is provided in connection with a customized therapy session delivered by the system of the present invention;

DETAILED DESCRIPTION OF THE INVENTION

Figure 2:
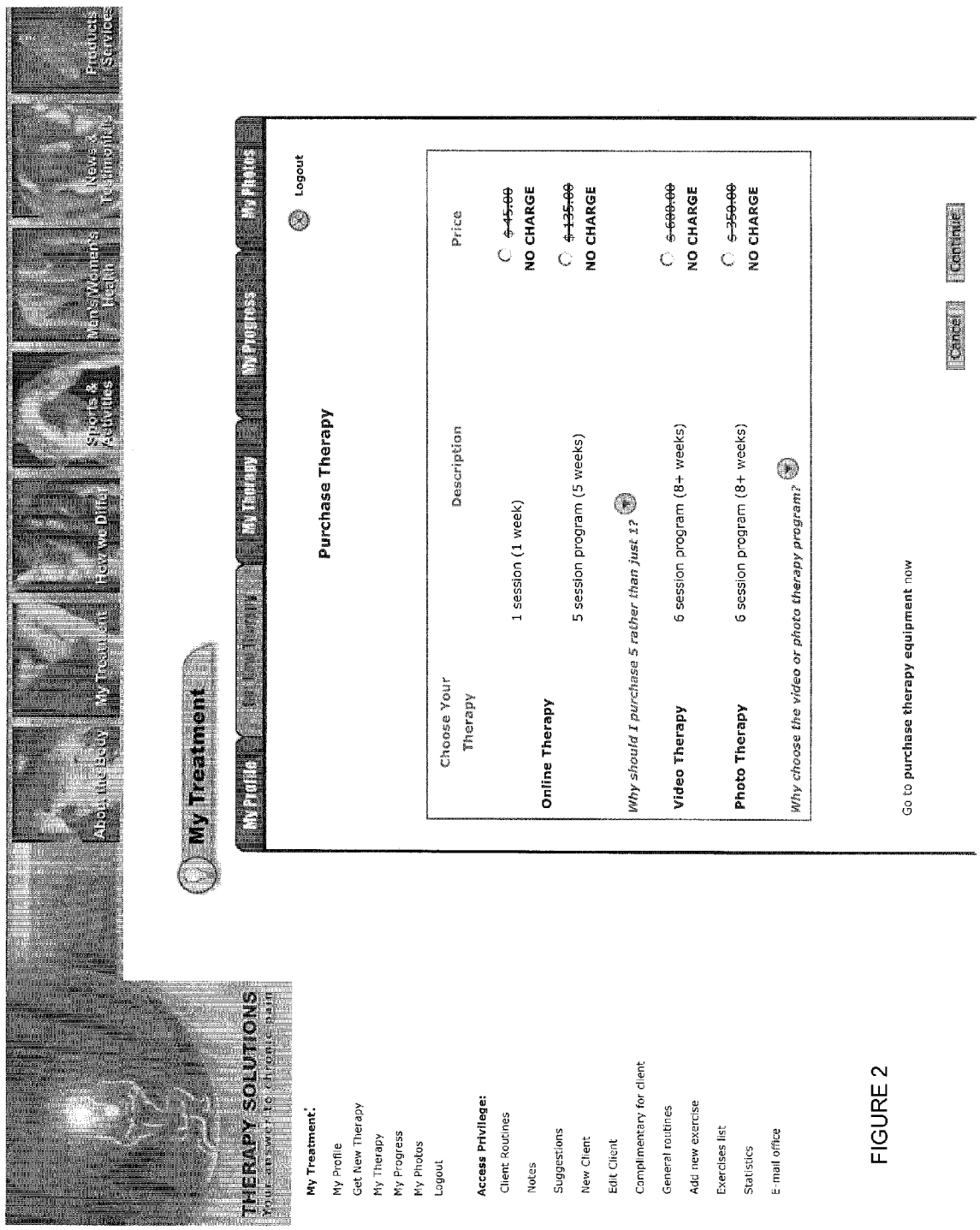
FIG. 2 is a screenshot representing a sample of a therapy selection screen in the system of the present invention.

As was stated above, the present invention is generally directed to an interactive method and system that enables a user to implement customized therapy routines without professional intervention. The method and system of the present invention is an innovative technique through which a user is enabled to evaluate and treat physical pain using a customized regimen that is provided via a computer interface and is typically delivered using electronic content delivery technologies such as the Internet and email.

The goal of the present invention is to deliver a customized therapy routine directly to a user in manner that allows the user to implement the therapy through an interface that assists the user in completing the therapy routine while also providing the user with meaningful feedback and progress tracking. The method of providing a user with a customized pain management therapy routine as disclosed in the present invention generally includes the establishment of a user account. With the user account established, a user is presented with an interactive interface that in turn prompts a user to provide personal information regarding their physical attributes and directs the user to complete an initial evaluation to obtain information regarding the user's physical condition, activity level, anatomical posture and pain symptoms. All of the personal information and the initial evaluation obtained from the user is then stored in the user account. Based on the information, the system performs an electronic analysis to assess the user's needs and to create and deliver a therapy session to the user based on the user's stated or identified needs. For the purpose of monitoring progress and providing the user with feedback, the user's progress is periodically monitored and the user is prompted to complete follow-up evaluations that are in turn compared to the previously entered evaluations in order to track the user's progress and to graphically present the progress as compared to the initial evaluation. Furthermore, progress evaluations must be completed and submitted by the individual in order that follow-up therapy sessions are delivered, which are automatically created and released by the system.

Figure 1:
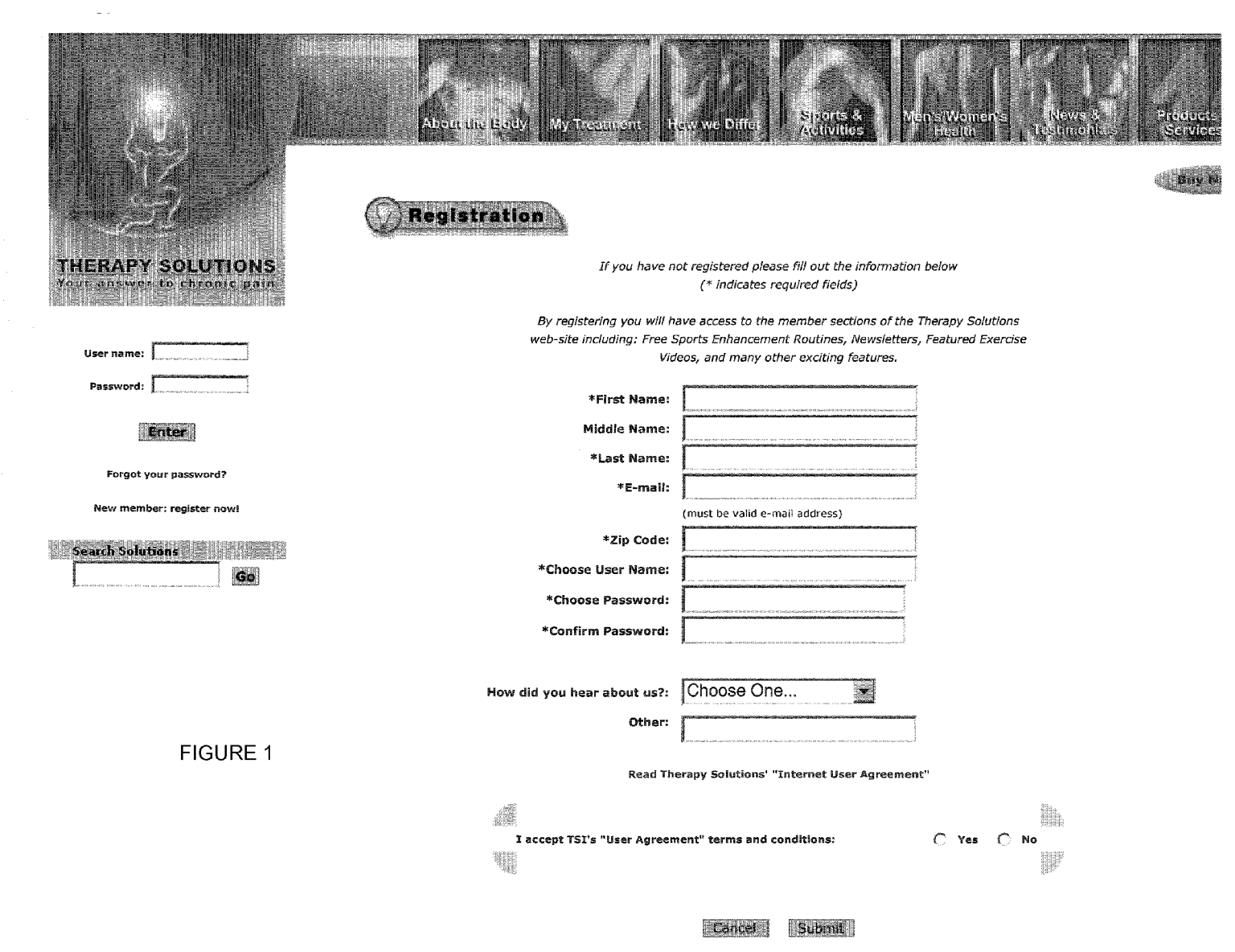

Turning now to the figures, FIG. 1 depicts a screenshot that represents an initial user input screen that is employed for establishing a user account. It should be appreciated that the method of the present invention may be implemented in a number of different variations, all of which are intended to fall within the scope of the present invention. Preferably, the system for implement the method of the present invention is hosted on a computer that is connected to and accessible through an electronic network such as the Internet or any other suitable wide area, accessible network. The user then accesses and interacts with the system via a local terminal for the purpose of inputting user information, obtaining their recommended therapy and following up with subsequent therapy sessions and evaluations. The general intent only requires that the system be provided and accessible by the user without the need for an intermediary or professional to input and maintain the user data.

Figure 3:
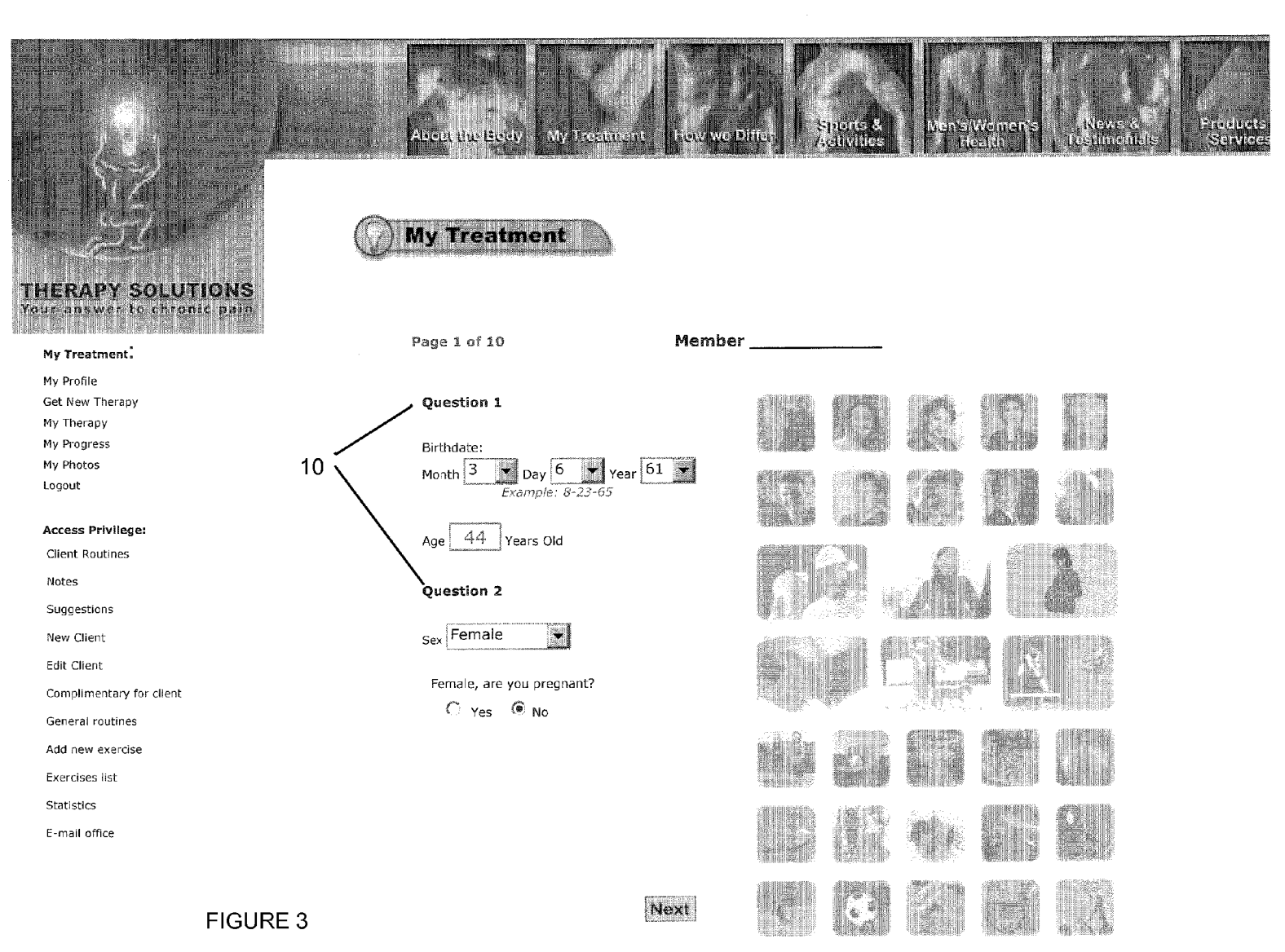
Figure 5:
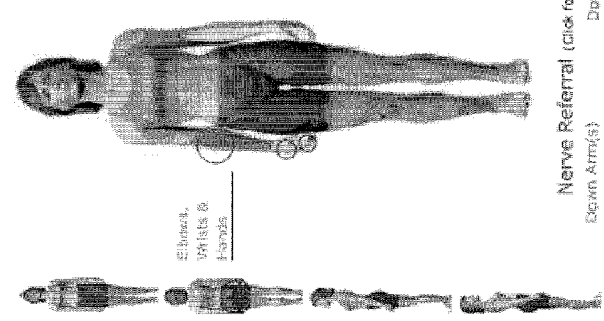
Figure 6:
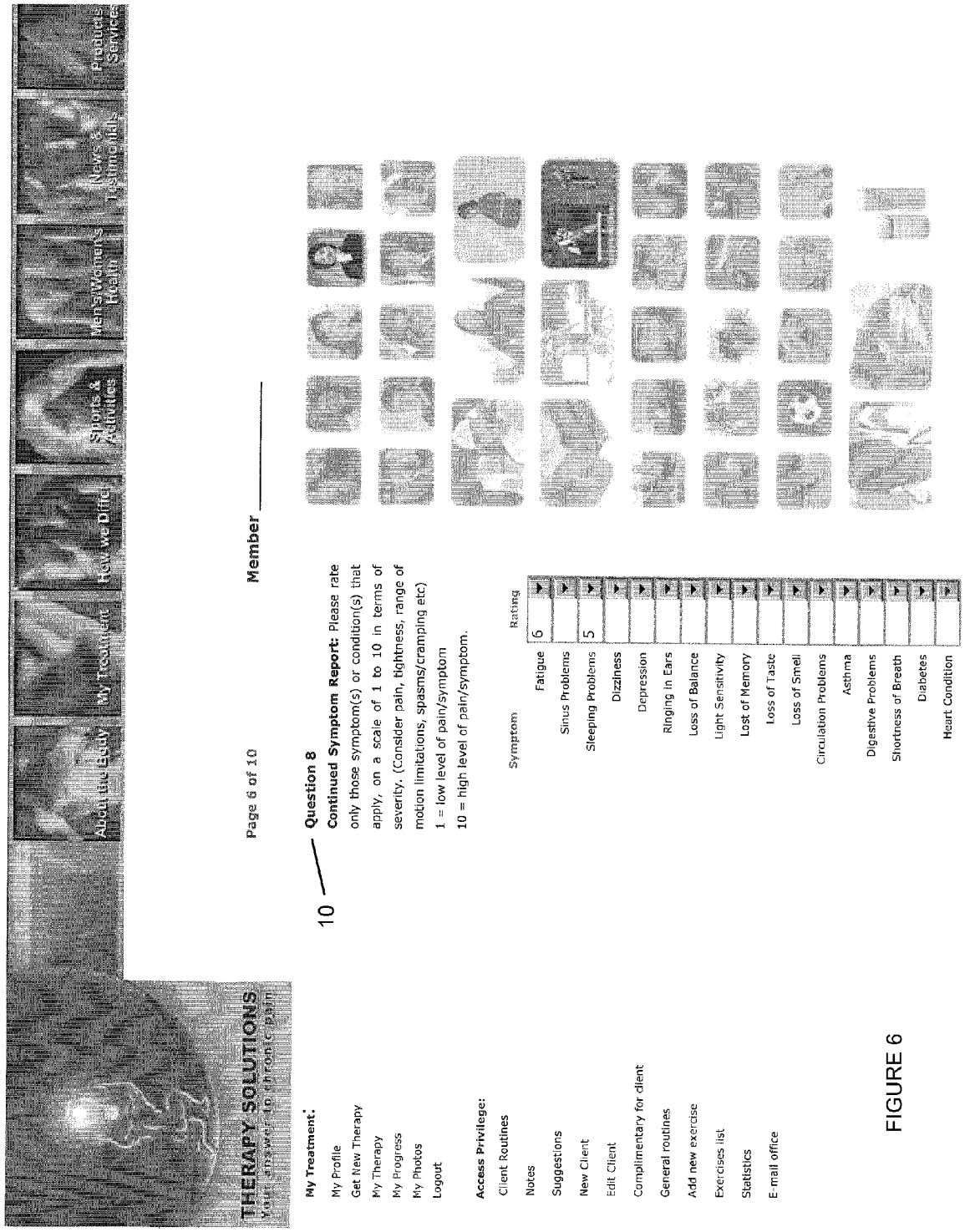
Figure 7:
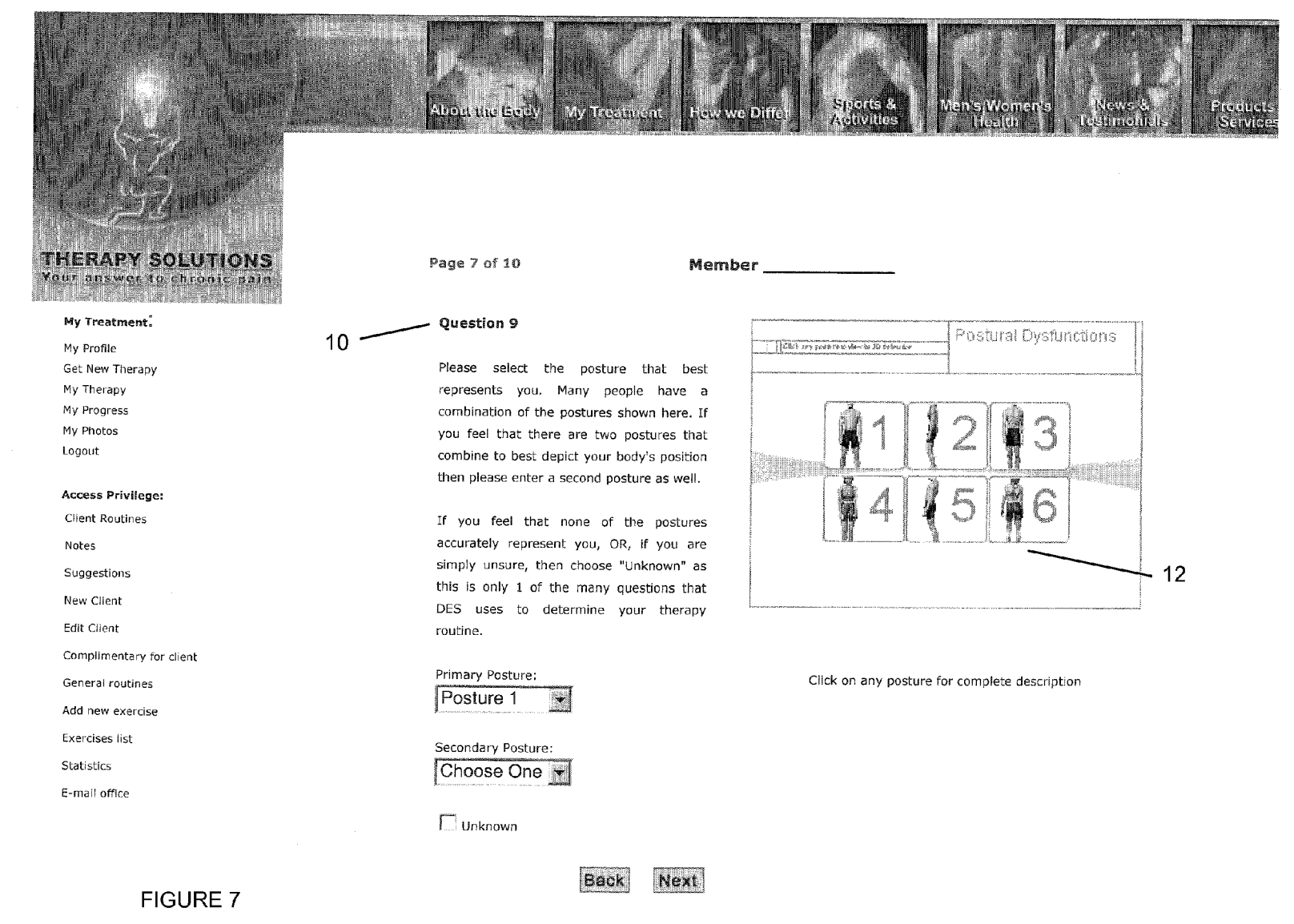

Once the user account has been established, the user then identifies the type of therapy that they wish to obtain. A sample of an interface screen for making this selection is depicted at FIG. 2. With the user account established, the basic user information entered and the user's therapy preferences identified, the system then prompts the user to respond to a number of questions 10 regarding their physical condition, activity level, anatomical posture and pain symptoms. FIG. 3 for example depicts questions 1 and 2 of a sample questionnaire directed at obtaining the user's age and gender while FIG. 4 depicts a question 10 for identifying the physical activities in which the user participates. FIGS. 5 and 6 include questions 10 that are directed at assisting the user identify the various areas of the body where the user is suffering pain or other symptoms and FIG. 7 provides the user with exemplar posture images 12 that allow the user to best identify their particular posture type and enter it into the system. The system also includes a feature whereby a user may upload self created images of their own body in order to directly evaluate their own posture as will be described more fully below. The system then asks the user to complete an initial evaluation regarding their assessment of their current fitness levels and the severity of their symptoms. After all the information obtained, it is stored in the user account to create a reference point from which the evaluation process will begin.

After the user completes the questions and provides the system with all of the information needed to evaluate the user's complaint and symptoms, the system immediately processes the information and evaluates the user's therapy needs without any input from an individual. Using a series of algorithms that review and analyze the responses provided by the user, the system selects a coordinated series of predefined therapy routines each consisting of predefined exercises and specs of each exercise (i.e. sets, repetitions, time) specifically for each routine, all designed to systematically correct posture deviations, muscular imbalances and biomechanical compensations and to relieve the user's symptoms. Once the processing is completed and the recommended therapy is identified then the system notifies the user that the first therapy session is available for their review. This process only takes seconds and is therefore delivered immediately to the user. Follow up reminder and engagement notifications are also distributed via email. The user can log in at anytime and view the most current session as well as all archived sessions. All multimedia pertaining to the specific personalized routines is stored and the user can view or print out the instructions for their therapy session.

The therapy sessions are delivered to the user in the form of recommended exercises that are to be completed by the user. The exercises 14 are presented, as is generally shown in FIG. 8, using a representative photograph depicting the proper form to be used when completing the exercise 14 as well as text providing the user with instructions for completing the exercise 14. A user can also click on the photograph representing the exercise 14 to view a video clip of a therapist performing the exercise properly. An initial therapy session may include several such exercises 14 that were identified by the system to particularly address the symptoms and muscular conditions of the user. The intent is that based on user responses to an interactive questionnaire, the system automatically evaluates the user's complaint and provides a tailored custom therapy session that the user implements in a self directed fashion.

Figure 9:
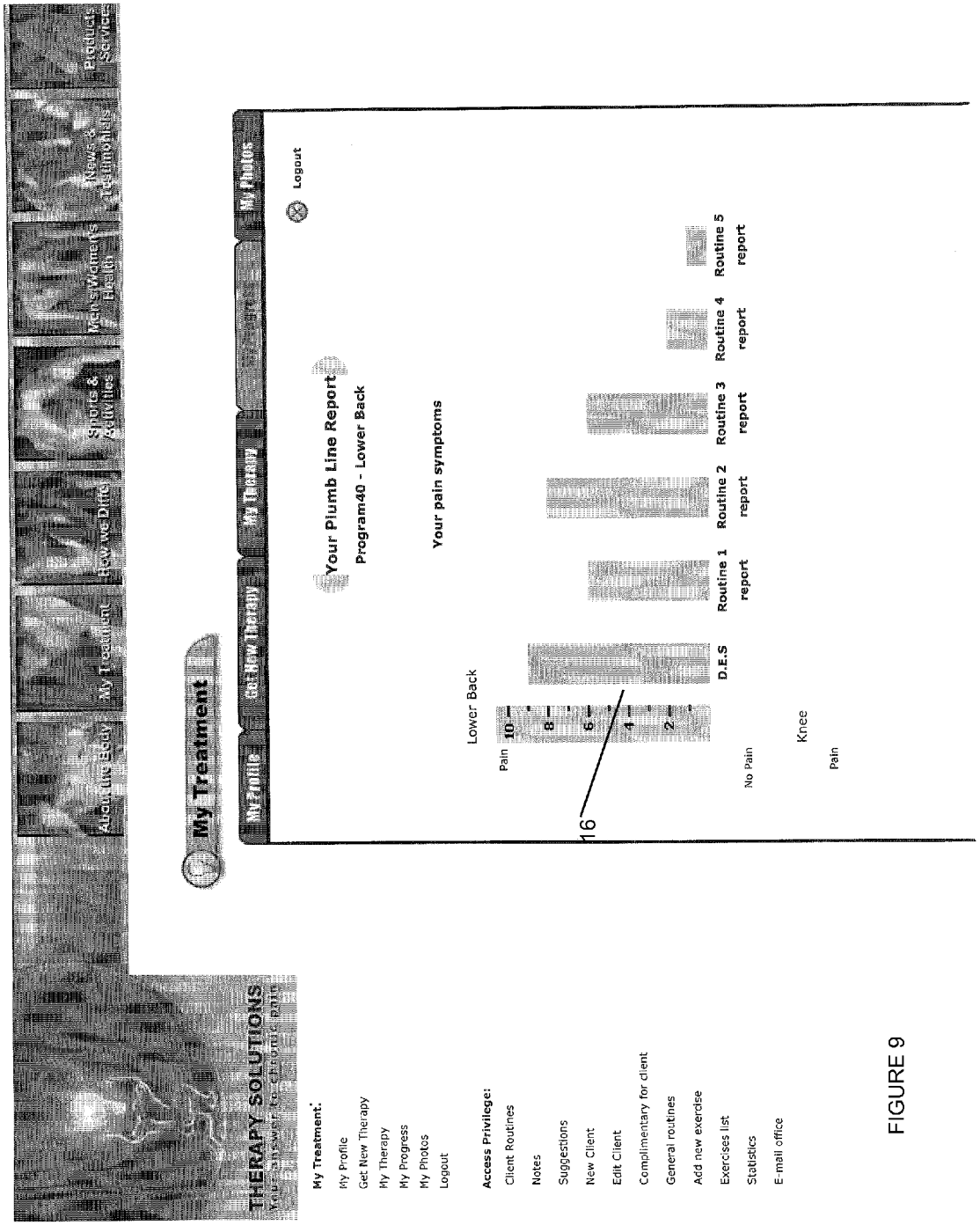
FIG. 9 is a screenshot representing a sample graphic depiction of the user's progress while implementing the therapy sessions via the system of the present invention.

The system is also configured to provide the user with updated therapy sessions as they progress through the automated system, monitor the user's progress with the therapy and obtain feedback from the user. In this manner, the system of the present invention automatically sends emails to the user to confirm that the previous therapy session has been viewed and completed. The follow-up emails also direct the user to interactively step through the same series of online evaluation questions asked in the initial evaluation to complete an updated evaluation. Once this information is collected, a new therapy session is delivered, and all information is stored in the user account alongside the user's initial evaluation whereby the results of the updated evaluation can be compared to the results of the initial evaluation and depicted graphically 16 such as is shown in FIG. 9. The reminder may be sent for example, once per week for the entire duration of the overall therapy, but if the user does not complete the first evaluation report at the beginning of the second week then the clock of releasing follow up reminders is paused until the user completes and continues into their next therapy session. The purpose of this is to replicate the process of face-to-face therapy sessions whereas an individual only receives new routines once their input is given and the assessment is made. In this manner, as the user proceeds through the sequential therapy sessions and periodically updates the evaluations they receive immediate feedback in a form of a new therapy session, further instructions, and an update regarding their overall progress towards their goal of living pain free.

Figure 10:
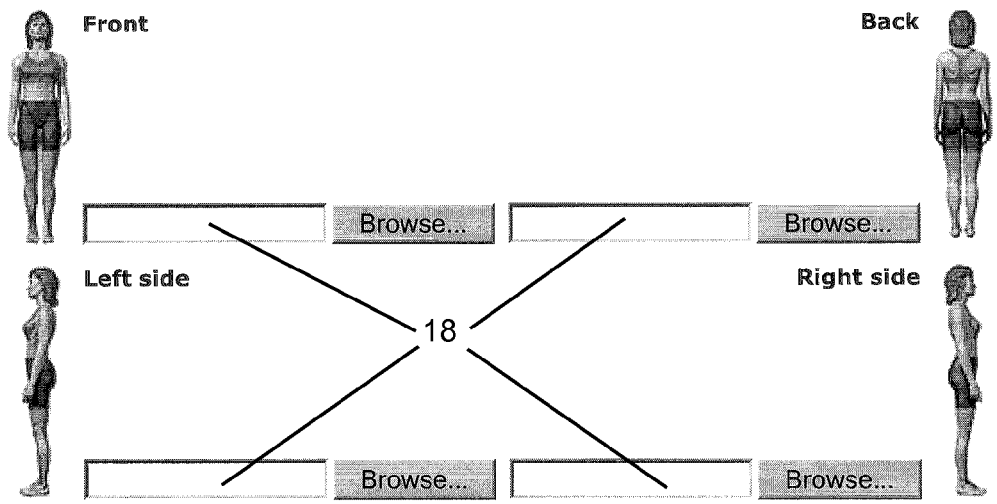
FIG. 10 is a screenshot representing a sample input screen for uploading user prepared images in the system of the present invention.

The method and system of the present invention also includes another feature not previously available in prior art evaluation systems. Specifically, the method and system of the present invention employs a technology that replicates the process of in-clinic and video therapy programs typically offered only at a therapy facility. The present system provides a unique method of evaluating the user's posture by allowing a user to upload predefined pictures and to manipulate a posture alignment guide tool to visually identify misalignment of the body and for comparison of posture before and after treatment. In this manner, the present invention provides the user with a guide that the user follows to create a set of images that are compatible with the system. The user then employs the interface 18 as depicted at FIG. 10 to upload their pictures into the system.

Figure 11:
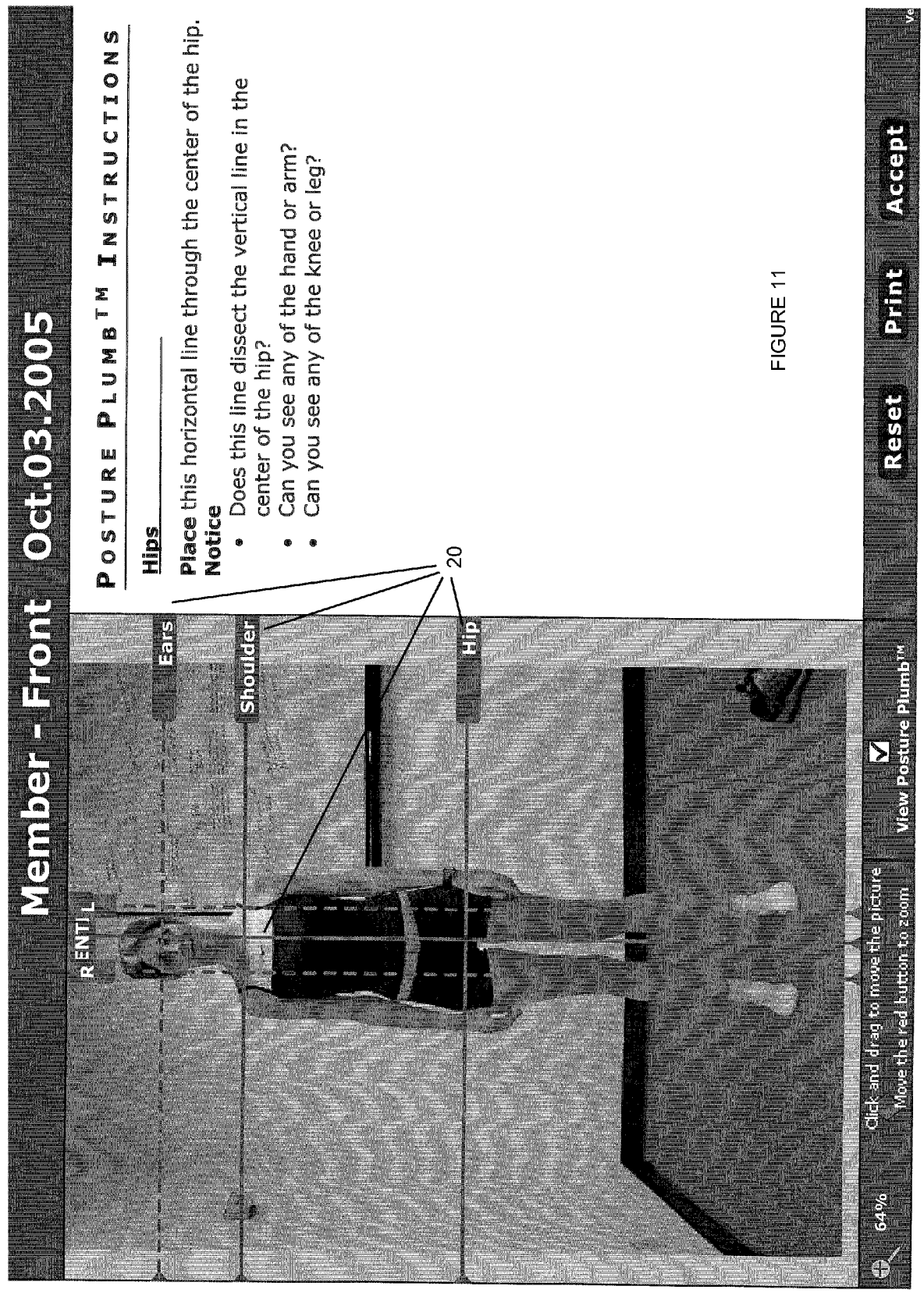
FIG. 11 is a screenshot depicting interactive posture alignment guides in overlying relation with a user uploaded image.

The system superimposes alignment guides 20, as are shown in FIG. 11, onto each of the uploaded pictures that are fully interactive allowing the user to move the alignment guides 20 to correspond to their personal images. The interactive alignment guides 20 can be moved by the user to visually identify the locations of improper posture and body position. The alignment guides 20 include a centerline, left and right vertical hip lines, an ear line, a shoulder line and a horizontal hip line. When a user places the cursor on one of the lines 20, the line 20 activates and can be moved. Further, as the line 20 is activated the interface displays instructions of exactly where to put the line on the photo and what to look for in the photo to identify problem areas. Photos can be resized (zoom) and dragged to a central position for proper alignment. In this manner, the uploaded body images in the method of the present invention may be either photographs or video clips. This also allows for the user to purchase photo and video therapy sessions, wherein the user uploads a series of photos or videos (prepared according to instructions provided by the system) which are evaluated by an anatomical specialist, who then prepares a personalized therapy program to correct the problems identified in the photos or video. In all other respects the therapy delivery and follow up proceeds as described above.

Figure 12:
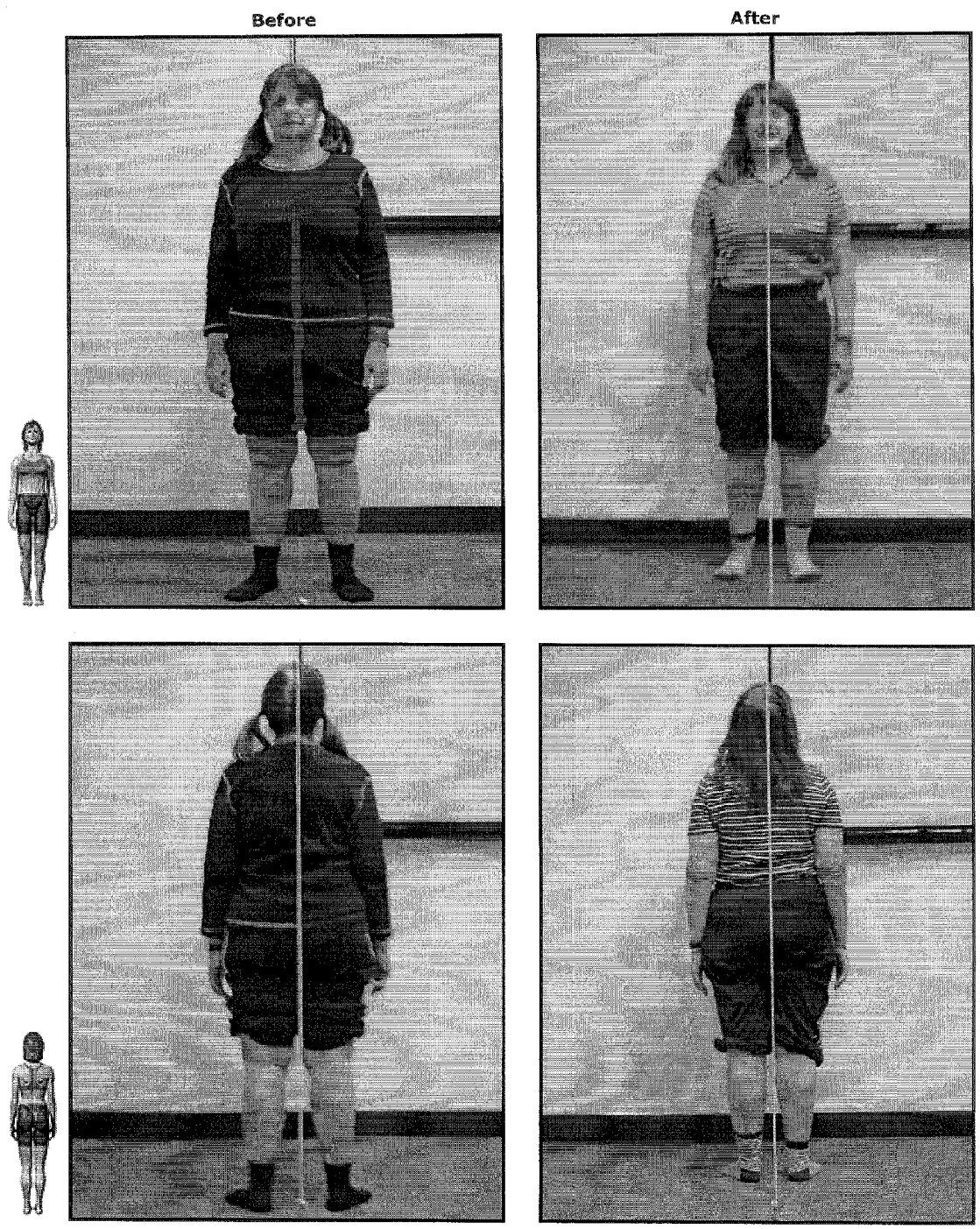
FIG. 12-13 are screenshots representing a side-by-side comparison of user uploaded images from before and after implementation of the therapy sessions.
Figure 13:
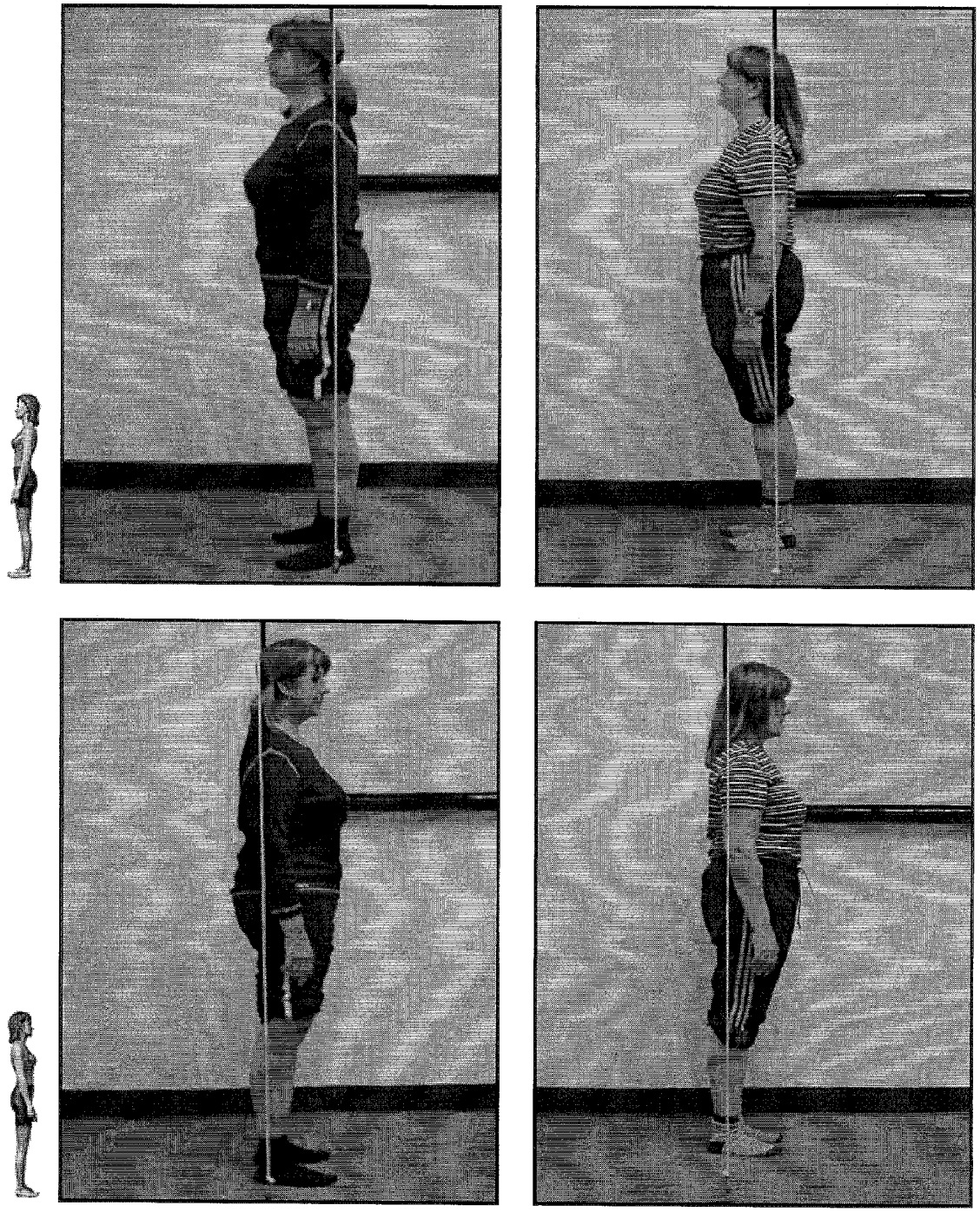
Figure 14:
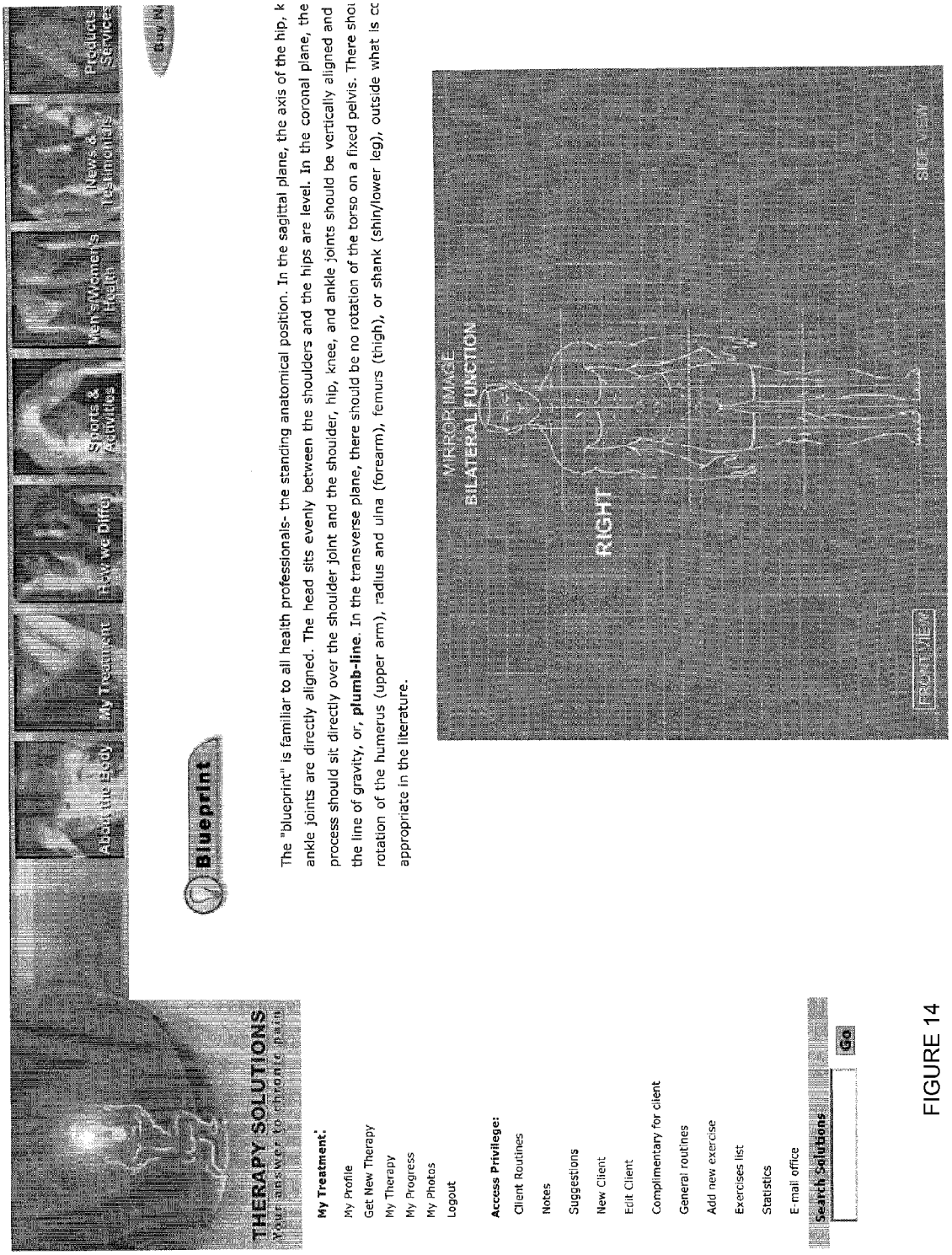
FIG. 14 is a screenshot representing a preprepared image depicting correct posture.

The system also stores the user pictures into the user account as they are uploaded and preserves them for comparison and tracking of progress. In this manner images from before and after therapy sessions can be compared in a side-by-side manner to provide the user with visual feedback regarding their progress through the therapy sessions. Such a side-by-side comparison is displayed in FIGS. 12 and 13. Finally, the uploaded images may be displayed in connection with preprepared images stored within said interface and depicting correct posture, such as is shown ion FIG. 14, wherein said user can observe their body posture as compared to correct body posture.

In a similar manner, the user can upload a video clip of them walking, in accordance with the directions given to walk to and from the camera with differing arm positions, backwards, and sideways, and the uploaded video triggers a practitioner to evaluate the video and then upload the appropriate therapeutic regimen.

Given the above description, in one example a proprietary system architecture for implementing the method and system is set forth in detail in the context of the P360™ ModuleBase™ Technology (P360™ and ModuleBase™ are trademarks of Therapy Solutions, Inc.). P360™ uses a proprietary architecture based on a unique structure: ModuleBase™. ModuleBase™ has a similar architecture to the traditional "database", but is vastly more capable and complex. The P360™ ModuleBase™ contains a large number of software modules designed to enhance existing modalities. The P360™ ModuleBase™ is vitally critical to the delivery of therapeutic solutions to targeted health care and fitness markets from highly safe and secure centralized facilities.

P360™ has been strategically packaged in multiple ways, in order to better deliver benefits, services, and data mining capabilities to multiple product-market pairings. The plan is to build up the P360™ ModuleBase™ in order to create an ever-increasing number of market-specific product offerings. In this context, the applicant utilizes P360™ to deliver its own APEX™, PTEX™ and FITEX™ products as described above and plans to use it for delivering all its other future products.

The following are brief descriptions of the modules currently available through the company's P360™ ModuleBase™ Technology:

(a) iView™ Personal Image Analyzer—Uploads pictures, virtual plumb line, recall, comparison, zoom, analysis, dated archive.

(b) Chart24™ Statistics Configurator—Tracks and provides comprehensive automated data collection of aggregate health metric results and usage trends including symptom, pain intensity, age, gender, activity level, locale, days off, medication use, etc. Collects, analyzes, graphs, and disseminates data depending on report parameters.

(c) Wizard Mailer™ Automated, time-triggered personalized communication with users, ensuring user compliance with prescribed therapy routines. Email database can be customized and personalized at any level of deployment.

(d) DES™ Digital Evaluation System—Internal routine evaluation engine that drives APEX™.

(e) Symptom Educator™—User friendly and visually stimulating process of choosing the area of pain on 3D interactive, rotating male or female bodies to learn how pain is associated to the kinetic chain, how that can affect treatment options and how lifestyles can be changed.

(f) Posture Educator™—Educates users and solidifies the customer relationship. 6 Postural descriptions using 4 body-position Flash movies.

(g) Dynamic Archiver™—Simple, quick referencing environment for all existing and future programs for users to access 24/7. Archive is multimedia ready.

(h) Coach Care™—Specific written communication support for AAT™, APEX™, P360™ and telephonic support for escalated needs in each market pairing.

(i) Personalized Regimen Builder™—Limitless personalization in building wellness programs. Existing templates jumpstart detailed customizations.

(j) Pain Advisor™—Interactive educational series of short instructions to self analyze posture and pain relationship, according to symptom region of the body.

(k) Automated Correction of Exercises™—System feedback monitor loop that interacts directly with each user's input in the APEX™ system including all progress evaluation reports. Makes exercise substitutions and adjustments as deemed necessary by the rules associated in the algorithms. (iView™, Chart24™, WizardMailer™, DES™, Symptom Educator™, Posture Educator™, Dynamic Archiver™, Coach Care™, Personlized Regimen Builder™, Pain Advisor™, and Automated Correction of Exercises™ are all trademarks of Therapy Solutions, Inc.).

It can therefore be seen that the present invention provides a novel method and system for delivering customized therapy sessions to address specific user symptoms in a cost effective and efficient manner that also dramatically reduces the need for costly therapist involvement. Further, the present invention provides an automated online system whereby a user can upload images and interactively evaluated their posture thereby allowing them to identify various posture defects and misalignments as was previously available only through an office visit with a professional therapist. For these reasons, the instant invention is believed to represent a significant advancement in the art, which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed:

1. A self-administered, automated method for providing a user with a customized physical therapy routine to treat pain:
    providing a host computer system accessible through an electronic network, said host computer system being configured with software effective for receiving personal information from a user and automatically generating a customized physical therapy routine based on said personal information;
    establishing a user account on said host computer system through a computer interface connected to said electronic network;
    building a user profile associated with said user account through an automated interactive questioning process controlled by said software on said host system, said software automatically prompting said user through said computer interface to input personal information including personal data, physical condition, activity level, anatomical posture and pain symptoms, said step of building said user profile being completed by said user without an intermediary or professional therapist, and without the need of any measured performance based data,
    said input of anatomical posture comprising the steps of presenting to said user a plurality of images depicting various postural dysfunctions, and prompting said user to select at least one image that best represents the user's posture,
    said input of pain symptoms comprising the steps of presenting to said user an image of a human body, and prompting said user to select an area of said human body where pain symptoms exist, and further prompting said user to input a pain level;
    storing said personal information in said user account;
    automatically generating an initial evaluation based on said personal information;
    automatically generating an initial customized physical therapy routine based on said personal information and said initial evaluation;
    providing said initial customized physical therapy routine to said user immediately through said computer interface;
    monitoring the user's progress by automatically prompting said user to enter updated personal information;
    automatically generating a follow-up evaluation based on said updated personal information;
    automatically generating an updated customized physical therapy routine based on said updated personal information and said follow-up evaluation;
    providing said updated customized physical therapy routine to said user immediately through said computer interface;
    tracking a user's progress wherein said software automatically compares results from said follow-up evaluation with said initial evaluation; and
    graphically presenting said progress to said user through said computer interface.

2. The method of claim 1, wherein said step of inputting personal information including personal data, physical condition, activity level, anatomical posture and pain symptoms comprises:
    generating a first set of user-created images of said user's body;
    uploading said first set of user-created images of said user's body via said computer interface;
    displaying said user-created images to said user through said computer interface;
    prompting said user through said computer interface to superimpose alignment guides over said first set of user-created images, whereby said user can visually self-evaluate their body posture by comparing said first set of user-created images with said alignment guides.

3. The method of claim 2, wherein said step of tracking a user's progress includes generating a second set of user-created images of said user's body, uploading said second set of images of said user's body after completing said updated customized physical therapy routine, prompting the user through said computer interface to superimpose alignment guides over said second set of user-created images, and comparing the second set of user-created images to said first set of user-created images to identify improvements in posture.

4. The method of claim 2, wherein said alignment guides can be repositioned relative to said first set of user-created images.

5. The method of claim 2, wherein said user-created images are prepared by said user based on instructions obtained from said host computer system.

6. The method of claim 2, wherein said step of displaying said user-created images further comprises displaying said user-created images in conjunction with preprepared images depicting correct posture, wherein said user can observe and self-evaluate their body posture as compared to correct body posture.

7. The method of claim 2 wherein said user-created images are photographs.

8. The method of claim 2, wherein said user-created images are video segments.

9. The method of claim 1, wherein said steps of providing said initial customized physical therapy routine and said updated customized physical therapy routine to said user each comprise:

providing video clips depicting exercises to be completed by said user.

10. The method of claim 1, wherein said user is provided with an updated customized physical therapy routine once per week.

11. The method of claim 1 wherein said step of input of anatomical posture includes prompting the user to select a second image which, when combined with the first image best represents the user's posture.

12. The method of claim 1 wherein said step of input of pain symptoms includes prompting the user to select a second area of said human body where pain symptoms exist, and further prompting said user to input a pain level.

* * * * *